United States Patent [19]

Daute et al.

[11] Patent Number: 5,470,493
[45] Date of Patent: Nov. 28, 1995

[54] PROCESS FOR SOFTENING FABRICS BY CONTACTING THEM WITH A THIODIGLYCOL DERIVATIVE

[75] Inventors: Peter Daute, Essen; Ingo Wegener, Duesseldorf; Alfred Meffert, Monheim; Faize Berger, Duesseldorf, all of Germany

[73] Assignee: Henkel Kommanditgesellschaft auf Aktien, Duesseldort, Germany

[21] Appl. No.: 290,880
[22] PCT Filed: Feb. 10, 1993
[86] PCT No.: PCT/EP93/00323
§ 371 Date: Oct. 18, 1994
§ 102(e) Date: Oct. 18, 1994
[87] PCT Pub. No.: WO93/16989
PCT Pub. Date: Sep. 2, 1993

[30] Foreign Application Priority Data

Feb. 19, 1992 [DE] Germany .................. 42 04 885.0

[51] Int. Cl.⁶ .................. C07C 317/18; C11D 3/00
[52] U.S. Cl. .................. 252/8.7; 252/8.9; 8/115.51; 568/27; 568/28
[58] Field of Search ........ 252/8.7, 8.9; 8/115.51; 568/27, 28

[56] References Cited

U.S. PATENT DOCUMENTS

| | | | |
|---|---|---|---|
| 3,299,145 | 1/1967 | Chang | 568/32 |
| 3,627,845 | 12/1971 | Hickner et al. | 568/45 |
| 4,042,632 | 8/1977 | Hofer, Sr. et al. | 568/29 |
| 4,413,998 | 11/1983 | Guth et al. | 252/8.7 |
| 5,308,512 | 5/1994 | Stoll et al. | 252/8.7 |

FOREIGN PATENT DOCUMENTS

| | | |
|---|---|---|
| 2334899 | 1/1974 | Germany . |
| 3604039 | 8/1987 | Germany . |
| 3936862 | 5/1991 | Germany . |
| 4021694 | 1/1992 | Germany . |
| 1097396 | 1/1968 | United Kingdom . |

OTHER PUBLICATIONS

Journal of the American Chemical Society, vol. 110, No. 20, 28 Sep. 1988, Gaston, Pa. US pp. 6840–6845 J.–H. Fuhrhop et al. "A Macrocyclic Tetraether Bolaamphiphile and a Oligoamino a, w–Dicarboxylate Combine to Form Mono-layered, Porous Vesicle Membranes, which are Reversibly Sealed by EDTA and Other Bulky Anions".

Primary Examiner—Stephen Kalafut
Assistant Examiner—James M. Silbermann
Attorney, Agent, or Firm—Ernest G. Szoke; Wayne C. Jaeschke; Real J. Grandmaison

[57] ABSTRACT

A fabric softening composition containing a thiodiglycol derivative corresponding to formula I $$R^1-O-(C_2H_4O)_x-(C_2H_4-SO_z-C_2H_4-O)_w-(C_2H_4-O)_y-R^2 \quad (I)$$

wherein $R^1$ and $R^2$ are the same or different and represent linear or branched alkyl or alkenyl groups containing 6 to 30 carbon atoms or hydrogen, $x+y=0$ to 20, w is 1 to 5, and z is 1 or 2.

8 Claims, No Drawings

PROCESS FOR SOFTENING FABRICS BY CONTACTING THEM WITH A THIODIGLYCOL DERIVATIVE

BACKGROUND OF THE INVENTION

1. Field of the Invention

This invention relates to thiodiglycol derivatives, to their production by reaction of thiodiglycol with alcohols in the presence of acidic compounds and subsequent oxidation to the sulfoxide and/or sulfone. The invention also relates to the use of the described thiodiglycol derivatives for softening fabrics.

2. Discussion of Related Art

Domestic and institutional fabric softeners contain above all quaternary ammonium compounds, more particularly of the dimethyl distearyl ammonium chloride type or, more recently, compounds of similar structure containing one, two or three fatty acyloxyalkyl groups. On account of the increasing significance of stability in storage, viscosity characteristics and, in particular, biodegradability, above all in the case of highly concentrated fabric softeners, numerous proposals for replacing these components by nitrogen-free substitute compounds or corresponding systems have been published. These proposals encompass both inorganic components, more particularly inorganic insoluble components, such as layer silicate compounds (see, for example, DE-PS 23 34 899), and also selected organic components, for example disalts of long-chain α-sulfofatty acids, and combinations of such systems (see, for example, DE-PS 36 04 039).

Thiodiglycol derivatives, a process for their production and their use for softening fabrics are already known from German patent application DE 39 36 862 A1. However, on account of their limited solubility in water and their melting points, these compounds can only be made up into dispersions by laborious mixing. The ethoxylates of thiodiglycol derivatives described in German patent application P 40 21 694.2 represent an improvement in this regard. They are produced from α-olefin epoxides. Accordingly, the problem addressed by the present invention was to provide thiodiglycol derivatives suitable for softening fabrics using renewable raw materials, another problem addressed by the invention being to provide a process for the production of these compounds which would enable even relatively large quantities to be readily produced.

DESCRIPTION OF THE INVENTION

Accordingly, the present invention relates to thiodiglycol derivatives corresponding to general formula I:

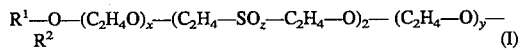
(I)

in which
$R^1$ and $R^2$ may be the same or different and represent linear or branched alkyl or alkenyl groups containing 6 to 30 carbon atoms or hydrogen,
$x+y=0$ to 20,
$w=1$ to 5,
$z=1$ or 2.

Accordingly, the thiodiglycol derivatives according to the invention are ethoxylated and non-ethoxylated bisethers of thiodiglycol sulfoxides or sulfones. Preferred thiodiglycol derivatives of formula I are those in which the substituents $R^1$ and $R^2$ derived from fatty alcohols are linear alkyl or alkenyl groups preferably containing 8 to 22 carbon atoms. Even though, in principle, $R^1$ and $R^2$ may be derived from fatty alcohols containing a uniform number of carbon atoms, it is best for reasons of cost to use naturally occurring fatty alcohol mixtures for the production of the thiodiglycol derivatives. Examples of inexpensively available fatty alcohol mixtures are coconut oil fatty alcohol, tallow fatty alcohol, palm oil and palm kernel oil fatty alcohol or even peanut oil fatty alcohol. The substituents $R^1$ and $R^2$ may be the same or different. However, since thiodiglycol derivatives containing the same substituents $R^1$ and $R^2$ are easier to produce, thiodiglycol derivatives in which $R^1$ and $R^2$ are the same are preferred. Where ethoxylated fatty alcohols are used as the starting material, correspondingly ethoxylated thiodiglycol derivatives, which are also effective fabric softeners, are obtained. Sulfoxides ($z=1$) or sulfones ($z=2$) are obtained, depending on the extent to which the thiodiglycol derivatives are oxidized. Thiodiglycol derivatives in which $z=2$, i.e. thiodiglycol sulfones, are preferred.

The present invention also relates to a process for the production of thiodiglycol derivatives corresponding to formula I, characterized in that thiodiglycol is condensed with alcohols corresponding to the formula $R^1$—OH and/or $R^2$—OH (where $R^1$ and $R^2$ are as defined above) or ethoxylates thereof in a molar ratio of 1:10 to 10:1 in the presence of acidic compounds at 120° to 200° C. with formation of ether groups, the water of reaction being removed, and the condensation products are oxidized in known manner to form the sulfoxide and/or sulfone. In one preferred embodiment of the process according to the invention, thiodiglycol is reacted with alcohol ethoxylates corresponding to the formula $R^1$—O—$(C_2H_4O)_xH$ and/or $R^2$—O—$(C_2H_4O)_yH$. The alcohol ethoxylates used best have relatively low degrees of ethoxylation, i.e. alcohol ethoxylates containing at most 10 moles of ethylene oxide per mole of alcohol are used. The reaction to form ether groups takes place particularly smoothly when acidic compounds are used as the catalyst. Accordingly, in another preferred process, acidic compounds, for example p-toluenesulfonic acid, sulfosuccinic acid or potassium hydrogen sulfate, are used as the catalyst. Particularly light-colored products are obtained when the condensation reaction is carried out in an inert gas atmosphere. Nitrogen is generally used as the inert gas.

The condensation reaction is followed by the oxidation reaction. In one preferred embodiment of the oxidation reaction, the oxidation is carried out with hydrogen peroxide, preferably in the presence of organic acids or solvents. The oxidation reaction with hydrogen peroxide is preferably carried out at a temperature in the range from 70° to 100° C.

The present invention also relates to the use of thiodiglycol derivatives corresponding to formula I for softening fabrics of natural and synthetic fibers and blends thereof. The dryness of the fabric to be treated is not an important factor in the use of the thiodiglycol derivatives in accordance with the invention. Accordingly, the desired softening effect occurs both in wet fabrics and in dry fabrics. The thiodiglycol derivatives according to the invention are generally absorbed onto the corresponding fabric both from aqueous solution and by forced application. The thiodiglycol derivatives according to the invention are preferably used after a washing or finishing process in an aqueous liquor containing from 0.1 to 1 g/l of the thiodiglycol derivatives corresponding to formula I. The aqueous liquors are best prepared by diluting aqueous dispersions and/or emulsions containing the thiodiglycol derivatives according to the invention. These dispersions contain thiodiglycol derivatives in quantities of from about 1 to 50% by weight and best in quantities of 5 to 20% by weight. In one important embodiment of the invention, the thiodiglycol derivatives are used in admixture with auxiliaries. Effective auxiliaries are surfactants in a broad sense. Suitable anionic surfactants are, for example, fatty alcohol sulfates and alkyl sulfonate salts, the alkali metal and alkaline earth metal salts and, above all, the sodium and magnesium salts having proved to be particularly effective. From the first group, the $C_{16-18}$ alcohol sulfate and related compounds may be mentioned as a particularly suitable mixing component. The second group includes, for example, α-sulfofatty acid methyl ester sulfonates, disalts of α-sulfofatty acids and comparable compounds. Suitable nonionic surfactants are both the conventional ethoxylates and also alkyl glycosides. The compounds mentioned may be used as auxiliaries in the production of the dispersions/emulsions in the same way as emulsifiers of other classes of compounds, for example glycerides, glycerol partial ethers and/or glycerol partial esters which, in addition to one or two free hydroxyl groups, contain relatively long-chain hydrocarbon radicals in the ether- or ester-forming functional substituents.

Preservatives, viscosity regulators, acidic compounds, dyes and fragrances may be used as further auxiliaries. The pH value of the dispersions/emulsions may be varied over a broad range, for example over the range from pH 4 to pH 11 and preferably over the range from pH 5 to pH 7.

In addition to the auxiliaries mentioned, the dispersions/emulsions to be used for softening fabrics may contain other constituents, for example solvents or stabilizers. The thiodiglycol derivatives corresponding to formula I are preferably used in admixture with solvents, dispersion aids, emulsifiers and/or stabilizers in quantities of 5 to 95% by weight and preferably in quantities of 20 to 70% by weight, based on the active-substance mixture, the thiodiglycol derivatives having to be present in finely dispersed form in order to obtain optimal effects.

Various thiodiglycol derivatives, their production and their use for softening fabrics are described in the following Examples which are not intended to limit the invention in any way.

EXAMPLES

EXAMPLE 1

This Example describes the preparation of a typical thiodiglycol derivative according to the invention. Other thiodiglycol derivatives according to the invention may be similarly prepared using various alcohols, optionally in various molar ratios with various quantities of hydrogen peroxide.

3787 g (14 moles) of stearyl alcohol, 855 g (7 moles) of thiodiglycol (Glyecin A, a product of BASF) and 11.4 g of p-toluenesulfonic acid monohydrate were weighed into a reaction vessel equipped with a stirrer and water separator and heated with stirring to around 170° C. over a period of 6 hours during which nitrogen was introduced. The course of the reaction was followed from the quantity of water separated. 4400 g of thiodiglycol distearyl ether was obtained in the form of a pale yellow-colored solid.

For oxidation to the sulfone, 1270 g of the thiodiglycol distearyl ether obtained as described above were heated to 80° C. and 433 g of 35% hydrogen peroxide were slowly added over a period of about 60 minutes. After stirring for 4 h at 90° to 98° C., the reaction product was repeatedly washed with hot water until no more peroxide could be detected in the washing water. The pale yellow solid product was then dried in vacuo at 120° C. 1244 g of the sulfone were obtained.

EXAMPLE 2

This Example describes the use and the testing of the thiodiglycol derivatives according to the invention.

Cotton terry swatches were hardened by one wash at 95° C. and five washes at 60° C. in a liquor containing 215 g of a phosphate-free detergent per 3.5 kg of terry swatches. The swatches were not prewashed. This hardened material was given a feel score of 0. Quantities of 60 g of hardened terry swatches were treated for 5 minutes in a Wacker machine with 600 g of an aqueous dispersion containing a mixture of 5% by weight of the sulfone obtained is described above and 4% by weight of sodium tallow alcohol sulfate (liquor ratio 1:10) in water with a hardness of 16° d. After drying, the softness of the terry swatches was evaluated by people skilled in the evaluation of softness. A feel score of 4 was awarded for a "very soft" feel. Terry swatches which had been treated with a liquor containing 3 g of the aqueous dispersion described above per liter were given a feel score of 3. Terry swatches which had been treated with a liquor having twice the concentration were given a feel score of 4.

Comparable results are obtained when n-octyl alcohol or a mixture of n-octyl alcohol with stearyl alcohol or behenyl alcohol was used instead of stearyl alcohol for forming the ether groups. An equally good result was obtained with a product where the alcohol was used in less than and more than equivalent quantity for forming the ether groups. The feel scores of the test fabrics thus treated were in the range from 3.0 to 3.4 for an in-use concentration of 3 g per liter.

EXAMPLE 3

7.5 g of a 30% solution of potassium hydroxide in methanol were added to 900 g of a mixture of cetyl alcohol and stearyl alcohol (1:1), followed by heating to 80° C. in an autoclave. At this temperature, the traces of methanol present were removed by evacuation and purging with nitrogen a total of five times. After the reaction temperature had been increased to 140° C., a total of 154 g of ethylene oxide was added in portions in such a way that the pressure in the reactor did not exceed $5.10^5$ Pa. On completion of the reaction, the reaction mixture was cooled to around 90° C. and was evacuated for 15 minutes to remove the traces of ethylene oxide still present. A colorless solid with an OH value of 185 was obtained.

Yield: 1061 g of fatty alcohol ethoxylate.

760 g of fatty alcohol ethoxylate, 153 g of thiodiglycol and 15 g of p-toluenesulfonic acid monohydrate were reacted as in Example 1 (4.5 hours, 160°–180° C., quantity of water separated 46 ml).

The reaction product was oxidized with 255 g of 35% hydrogen peroxide as in Example 1. Yield: 838 g, OH value: 24, acid value: 1.4.

EXAMPLE 4

1061 g of 2-hexyl decanol, 244 g of thiodiglycol and 3.6 g of p-toluenesulfonic acid monohydrate were reacted as in Example 1 (5 hours, 160°–170° C., quantity of water separated 66 ml).

The reaction product was oxidized with 393 g of 35% hydrogen peroxide as in Example 1. Yield: 1235 g, OH value: 54, acid value: 0.8.

EXAMPLE 5

1117 g of oleyl alcohol (iodine value 90–95), 244 g of thiodiglycol and 3.6 g of p-toluenesulfonic acid monohydrate were reacted as in Example 1 (5.5 hours, 160°–170° C., quantity of water separated 65 ml).

The reaction product was oxidized with 393 g of 35% hydrogen peroxide as in Example 1. Yield: 1222 g, OH value: 54, acid value: 0.2, iodine value: 76.

EXAMPLE 6

866 g of a technical alcohol mixture (5% $C_8$, 5% $C_{10}$, 50% $C_{12}$, 20% $C_{14}$, 10% $C_{16}$, 8% $C_{18}$), 269 g of thiodiglycol and 4.0 g of p-toluenesulfonic acid monohydrate were reacted as in Example 1 (6 hours, 160°–170° C., quantity of water separated 70 ml).

The reaction product was oxidized with 499 g of 35% hydrogen peroxide as in Example 1. OH value: 55, acid value: 0.6.

EXAMPLE 7

886.9 g of 1-hexadecene oxide and 315.3 g of thiodiglycol+2 EO (thiodiglycol reacted with 2 moles of ethylene oxide) were introduced into a reaction vessel together with 7.8 g of a 50% potassium hydroxide solution and traces of water present were removed by heating in vacuo to 100° C. The slightly exothermically reacting mixture was then heated under nitrogen to around 160° to 170° C. To monitor the reaction, the epoxide oxygen content of the reaction mixture was determined at regular intervals, an epoxide oxygen content of less than 0.3% being reached after a reaction time of 3 to 6 hours, indicating that the reaction was over. After cooling, the product was neutralized with an equivalent quantity of 90% lactic acid.

1100 g of the reaction product prepared as described above were heated to 80° C. and 153 g of 70% hydrogen peroxide were slowly added over a period of 60 minutes. During the subsequent reaction, the temperature was kept below 90° C. by cooling. For the after-reaction, the product was heated for 4.5 hours at 90° C. and then washed with hot water until the peroxide test in the washing water produced a negative result. The light yellow solid sulfone was then dried in vacuo at 120° C.
OH value: 149, acid value: 0.9.

EXAMPLE 8

611 g (5 moles) of thiodiglycol and 3.1 g of p-toluenesulfonic acid monohydrate were introduced into a reaction vessel equipped with a stirrer and water separator and heated to 140°–180° C. while nitrogen was passed through (3.5 h). The course of the condensation reaction was followed from the quantity of water removed (quantity of water removed 45 ml+30 ml of thioxane). After addition of 1353 g (4.5 moles) of stearyl alcohol, the reaction mixture was heated for another 3 h at 170° C. (quantity of water 80 ml).

The reaction product was oxidized with 895 g of 35% hydrogen peroxide as in Example 1. Yield: 1627 g, OH value: 16, acid value: 0.8.

EXAMPLE 9

651 g of octanol, 306 g of thiodiglycol and 4.6 g of p-toluenesulfonic acid monohydrate were reacted as in Example 1 (6 h, 160°–180° C., quantity of water separated 80 ml) and oxidized with 495 g of 35% hydrogen peroxide. Yield: 758 g, OH value: 36, acid value: 0.6.

We claim:

1. The process of softening fabrics comprising contacting said fabrics with a fabric softening composition comprising a thiodiglycol derivative corresponding to formula I

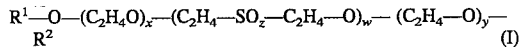

$$R^1-O-(C_2H_4O)_x-(C_2H_4-SO_z-C_2H_4-O)_w-(C_2H_4-O)_y-R^2 \quad (I)$$

wherein $R^1$ and $R^2$ are the same or different and represent linear or branched alkyl or alkenyl groups containing 6 to 30 carbon atoms or hydrogen, x+y equals 0 to 20, w is 1 to 5, and z is 1 or 2.

2. A process as in claim 1 wherein $R^1$ and $R^2$ are linear alkyl or alkenyl groups containing from 8 to 22 carbon atoms.

3. A process as in claim 2 wherein $R^1$ and $R^2$ are the same.

4. A process as in claim 1 wherein z is 2.

5. A process as in claim 1 wherein said thiodiglycol derivative is present in said composition in an amount of from about 1 to 50% by weight, based on the weight of said composition.

6. A process as in claim 1 wherein said thiodiglycol derivative is present in said composition in an amount of from about 5 to 20% by weight, based on the weight of said composition.

7. A process as in claim 1 wherein said composition further contains an auxiliary selected from the group consisting of anionic surfactants, nonionic surfactants, preservatives, viscosity regulators, solvents, dispersion aids, emulsifiers and stabilizers.

8. A process as in claim 1 comprising contacting said fabrics with an aqueous liquor containing 0.1 to 1 gram/liter of said thiodiglycol derivative.

* * * * *